United States Patent
Koehler et al.

(10) Patent No.: US 10,805,520 B2
(45) Date of Patent: Oct. 13, 2020

(54) SYSTEM AND METHOD USING ADJUSTMENTS BASED ON IMAGE QUALITY TO CAPTURE IMAGES OF A USER'S EYE

(71) Applicant: Sony Corporation, Tokyo (JP)

(72) Inventors: Thomas Koehler, Erlangen (DE); Marco Boegel, Erlangen (DE); Tobias Geimer, Erlangen (DE); Johannes Wendel, Erlangen (DE)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/034,505

(22) Filed: Jul. 13, 2018

(65) Prior Publication Data
US 2019/0028634 A1 Jan. 24, 2019

(30) Foreign Application Priority Data
Jul. 19, 2017 (EP) .................................. 17182213

(51) Int. Cl.
  *H04N 5/232* (2006.01)
  *A61B 3/00* (2006.01)
  *H04N 5/225* (2006.01)
  *A61B 3/11* (2006.01)

(52) U.S. Cl.
  CPC ....... *H04N 5/23219* (2013.01); *A61B 3/0025* (2013.01); *H04N 5/2256* (2013.01); *H04N 5/2257* (2013.01); *H04N 5/23222* (2013.01); *A61B 3/112* (2013.01)

(58) Field of Classification Search
  None
  See application file for complete search history.

(56) References Cited

U.S. PATENT DOCUMENTS

| | | | | |
|---|---|---|---|---|
| 7,377,643 | B1* | 5/2008 | Chock | A61B 3/14 351/205 |
| 7,401,920 | B1* | 7/2008 | Kranz | A61B 3/113 351/209 |
| 8,437,513 | B1* | 5/2013 | Derakhshani | G06K 9/00597 382/115 |
| 9,149,179 | B2 | 10/2015 | Barnard et al. | |

(Continued)

FOREIGN PATENT DOCUMENTS

| | | |
|---|---|---|
| JP | 2009-193198 | 8/2009 |
| WO | WO 2016/001868 A1 | 1/2016 |
| WO | WO 2016/161103 A1 | 10/2016 |

OTHER PUBLICATIONS

Ya-Ping Huang, Si-Wei Luo and En-Yi Chen, "An efficient iris recognition system," Proceedings. International Conference on Machine Learning and Cybernetics, Beijing, China, 2002, pp. 450-454 vol. 1.doi: 10.1109/ICMLC.2002.1176794 (Year: 2002).*

(Continued)

*Primary Examiner* — Jayanti K Patel
*Assistant Examiner* — Stefan Gadomski
(74) *Attorney, Agent, or Firm* — Xsensus LLP (57) ABSTRACT

A mobile system has a circuitry, which has a camera. The circuitry captures a plurality of images of a user's eye with the camera, determines based on at least one of the captured images of the eye, an image quality of at least one feature of the eye in the captured image, and outputs a user instruction for changing the image quality of the at least one feature of the eye.

22 Claims, 7 Drawing Sheets

(56) References Cited

U.S. PATENT DOCUMENTS

| | | | |
|---|---|---|---|
| 9,289,122 B2 | 3/2016 | Chinnock et al. | |
| 9,462,945 B1* | 10/2016 | Barriga | A61B 3/152 |
| 9,526,417 B1* | 12/2016 | Massetti | A61B 3/152 |
| 10,262,203 B2* | 4/2019 | Sung | G06K 9/00 |
| 2001/0026632 A1* | 10/2001 | Tamai | G06K 9/00 382/116 |
| 2005/0119642 A1* | 6/2005 | Grecu | A61B 3/113 606/5 |
| 2006/0008124 A1* | 1/2006 | Ewe | G06K 9/00597 382/117 |
| 2006/0098097 A1* | 5/2006 | Wach | G02B 27/0025 348/207.99 |
| 2006/0192868 A1* | 8/2006 | Wakamori | A61B 5/117 348/294 |
| 2007/0274570 A1* | 11/2007 | Hamza | G06K 9/0061 382/117 |
| 2009/0097715 A1* | 4/2009 | Cottard | G06K 9/00597 382/117 |
| 2010/0110378 A1* | 5/2010 | Cheng | A61B 3/15 351/208 |
| 2010/0183199 A1* | 7/2010 | Smith | G06K 9/00597 382/117 |
| 2010/0232655 A1* | 9/2010 | Hanna | G06K 9/00604 382/117 |
| 2010/0284576 A1* | 11/2010 | Tosa | G06K 9/0061 382/117 |
| 2010/0299530 A1* | 11/2010 | Bell | G06F 21/32 713/186 |
| 2011/0170068 A1* | 7/2011 | Dan-Gur | A61B 3/10 351/214 |
| 2011/0267447 A1* | 11/2011 | Su | G06K 9/0061 348/78 |
| 2012/0062720 A1* | 3/2012 | Choi | G06K 9/00604 348/78 |
| 2012/0102332 A1* | 4/2012 | Mullin | G06F 1/1626 713/186 |
| 2012/0148115 A1* | 6/2012 | Birdwell | G06K 5/00 382/116 |
| 2012/0212706 A1* | 8/2012 | Chou | A61B 3/0033 351/223 |
| 2013/0016274 A1* | 1/2013 | Matsuo | H04N 5/3696 348/345 |
| 2013/0083185 A1* | 4/2013 | Coleman, III | A61B 3/12 348/78 |
| 2013/0088583 A1* | 4/2013 | Northcott | G06K 9/00604 348/78 |
| 2013/0147603 A1* | 6/2013 | Malhas | G06K 9/00597 340/5.83 |
| 2013/0162798 A1* | 6/2013 | Hanna | A61B 3/14 348/78 |
| 2013/0162799 A1* | 6/2013 | Hanna | A61B 5/117 348/78 |
| 2013/0173750 A1* | 7/2013 | Carnevale | G16H 40/67 709/218 |
| 2014/0036229 A1* | 2/2014 | Hsu | A61B 3/12 351/206 |
| 2014/0072201 A1* | 3/2014 | Tilt | H04N 5/23293 382/140 |
| 2014/0268040 A1* | 9/2014 | Mujat | A61B 3/102 351/206 |
| 2014/0285436 A1* | 9/2014 | Wu | A61B 5/1116 345/156 |
| 2014/0341441 A1* | 11/2014 | Slaby | G06F 21/32 382/117 |
| 2015/0040212 A1* | 2/2015 | Kim | G06F 21/32 726/19 |
| 2015/0071503 A1* | 3/2015 | Prabhakar | G06K 9/6215 382/117 |
| 2015/0085253 A1 | 3/2015 | Walsh et al. | |
| 2015/0087924 A1* | 3/2015 | Li | A61B 3/0041 600/301 |
| 2015/0104087 A1 | 4/2015 | Katuwal et al. | |
| 2015/0124069 A1* | 5/2015 | Tsukamoto | G06K 9/00604 348/78 |
| 2015/0254508 A1* | 9/2015 | Kimura | G06K 9/00604 382/117 |
| 2015/0313462 A1* | 11/2015 | Reis | A61B 3/10 351/206 |
| 2016/0021294 A1* | 1/2016 | Tamer | H04N 5/23212 382/117 |
| 2016/0045108 A1* | 2/2016 | Wu | A61B 3/112 351/210 |
| 2016/0192873 A1* | 7/2016 | Kelly | A61B 5/00 351/209 |
| 2016/0320839 A1* | 11/2016 | Song | H04B 1/385 |
| 2016/0335475 A1* | 11/2016 | Krenzer | G06T 7/77 |
| 2016/0364609 A1* | 12/2016 | Ivanisov | G06K 9/4604 |
| 2016/0366317 A1* | 12/2016 | Ivanisov | G06K 9/00604 |
| 2016/0374594 A1* | 12/2016 | Garcia Molina | A61B 3/145 600/558 |
| 2017/0131765 A1* | 5/2017 | Perek | G02B 5/3083 |
| 2017/0146801 A1* | 5/2017 | Stempora | G06Q 10/063 |
| 2017/0164830 A1* | 6/2017 | Huang | G06T 7/13 |
| 2017/0188809 A1* | 7/2017 | Peddada | A61B 3/0025 |
| 2017/0347000 A1* | 11/2017 | Perna | G06F 21/32 |
| 2017/0374280 A1* | 12/2017 | Chan | H04N 5/23222 |
| 2018/0014725 A1* | 1/2018 | Bagherinia | A61B 3/0025 |
| 2018/0028058 A1* | 2/2018 | Saidman | A61B 3/14 |
| 2018/0032815 A1* | 2/2018 | Lee | G06K 9/00604 |
| 2018/0055357 A1* | 3/2018 | Meyerson | A61B 3/14 |
| 2018/0078134 A1* | 3/2018 | Katz | A61B 3/024 |
| 2018/0092534 A1* | 4/2018 | Nabhan | A61B 3/14 |
| 2018/0103839 A1* | 4/2018 | Kurtz | A61B 3/0008 |
| 2018/0116509 A1* | 5/2018 | Myung | A61B 3/10 |
| 2018/0125352 A1* | 5/2018 | Schmid | A61B 3/0041 |
| 2018/0144192 A1* | 5/2018 | Kim | G06F 21/32 |
| 2018/0255167 A1* | 9/2018 | Saito | G06K 9/00604 |
| 2018/0349682 A1* | 12/2018 | Wong | G06K 9/00906 |
| 2018/0365844 A1* | 12/2018 | Cai | G06T 7/248 |
| 2019/0028690 A1* | 1/2019 | Raghoebardajal | H04N 13/371 |

OTHER PUBLICATIONS

Luis J. Haddock et al. "Simple, Inexpensive Technique for High-Quality Smartphone Fundus Photography in Human and Animal Eyes", Journal of Ophthalmology, vol. 2013, 2013, 6 pages.

\* cited by examiner

SYSTEM AND METHOD USING ADJUSTMENTS BASED ON IMAGE QUALITY TO CAPTURE IMAGES OF A USER'S EYE

TECHNICAL FIELD

The present disclosure generally pertains to a mobile system and a method in the general field of eye imaging devices.

TECHNICAL BACKGROUND

Conventional eye imaging devices are typically based on, for example, using special designed retinal imaging equipment that enables manual eye examinations and has to be operated by professionals, such as a clinician, an ophthalmologist, etc. Such stationary cameras are currently used in clinical practice in which the retinal cameras are manually aligned relative to the eye.

Moreover, it is known that hand-held imaging devices exist that enable retinal screening, for example, a trained medical assistant takes digital images for evaluation.

Such a hand-held device can enable eye monitoring by a second person, for example, a clinician may determine temporal and/or structural changes on the eye of a patient. Moreover, an expert knowledge is required to manually compare captured images of the eye with a reference image. Additionally, the patient should visit the doctor's office on a regular basis.

However, in order to capture high quality images with such devices, the devices should be precisely aligned with respect to the user's eye by a second person, i.e. a clinician, an ophthalmologist, etc.

Although there exist techniques for capturing image of an eye by a mobile imaging device, e.g., by trained medical assistants, it is generally desirable to improve mobile devices, systems and methods for eye examinations.

SUMMARY

According to a first aspect the disclosure provides a mobile system including circuitry including a camera, the circuitry being configured to capture a plurality of images of a user's eye with the camera; determine, based on at least one of the captured images of the eye, an image quality of at least one feature of the eye in the captured image; and output a user instruction for changing the image quality of the at least one feature of the eye.

According to a second aspect the disclosure provides a method including capturing a plurality of images of a user's eye with the camera; determining, based on at least one of the captured images of the eye, an image quality of at least one feature of the eye in the captured image; and outputting a user instruction for changing the image quality of the at least one feature of the eye.

Further aspects are set forth in the dependent claims, the following description and the drawings.

BRIEF DESCRIPTION OF THE DRAWINGS

Embodiments are explained by way of example with respect to the accompanying drawings, in which.

DETAILED DESCRIPTION OF EMBODIMENTS

Figure 1:
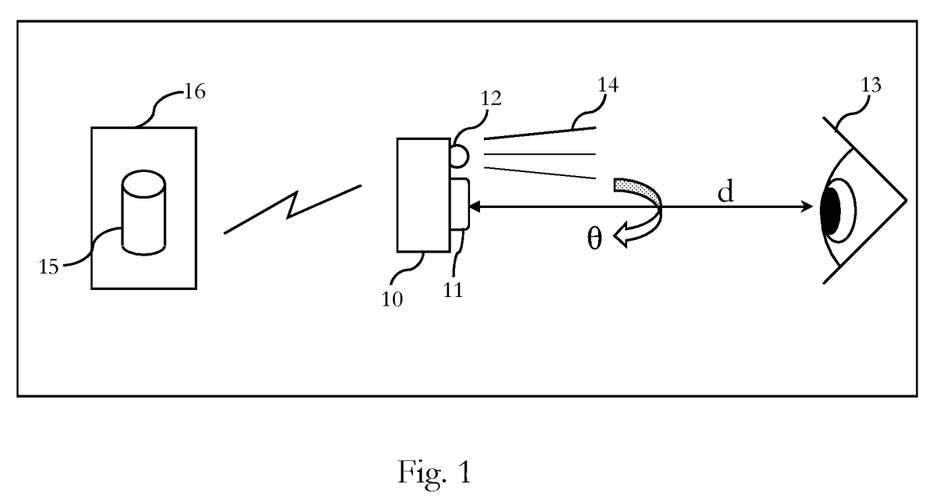
FIG. 1 illustrates an embodiment of a mobile device for capturing an image of a user's eye.

Before a detailed description of the embodiments under reference of FIG. 1 is given, general explanations are made.

As mentioned in the outset, generally it is known to perform an eye examination, for example, by a tele-medicine method in which a trained health specialist takes images of the patient's eye and transmits the images to a health center for evaluation.

However, currently capturing of the eye's image and monitoring of the eye is performed by a second person.

It has been recognized, for improved usability, e.g., such mobile devices should be operated by the user alone, such that a user is enabled to capture images of their own eye. Moreover, the mobile devices may be improved to, e.g., analyze the captured images.

Consequently, some embodiments pertain to a mobile system including circuitry including a camera, the circuitry being configured to capture a plurality of images of a user's eye with the camera; determine, based on at least one of the captured images of the eye, an image quality of at least one feature of the eye in the captured image; and output a user instruction for changing the image quality of the at least one feature of the eye.

The mobile system may include a mobile device, which may be a smartphone, a tablet computer, a digital camera, it may be a mobile imaging device, e.g., an eye imaging device such as an ophthalmoscope, a fundus camera, a mobile retinal camera system, or the like. The mobile system may include further devices in addition to the mobile device, such as a loudspeaker, display, or the like.

The circuitry may further include one or more processors, one or more microprocessors, dedicated circuits, logic circuits, a memory (RAM, ROM, or the like), a storage, output means (display (e.g. liquid crystal, (organic) light emitting diode, etc.)), microphone, loudspeaker, etc., an interface (e.g. touch screen, a wireless interface such as Bluetooth, infrared, etc.), etc., as it is generally known for typical mobile devices such as a smartphone, tablet PCs or the like.

The mobile device/system and/or its circuitry may further include one or more cameras. The camera may be located in the front or back side of the mobile device. In some embodiments the mobile device may include more than one camera, for example, it may be a dual camera mobile device, and may further include at least one camera on its front side and one camera on its back side. The camera may include a lens in which the light enters through the lens, a shutter release for enabling capturing an image, an aperture for controlling the image exposure, an image sensor for converting the optical image to an electronic signal, an analogto-digital converter, and may further include an auto setting for enabling automatic adjustment for different exposure parameters, and the like.

In some embodiments, the circuitry may further include a light adjacent to the camera for illuminating the user's eye during the time of capturing the image of the user's eye. The adjacent may be a flash light, it may be a LED sensor, or the like.

Moreover, the mobile device, and/or its cameras may further be configured to capture, for example, high resolution images, still images, videos, etc.

The mobile device may further include sensors, for example, for sensing audio (e.g. one or more microphones), for sensing still images or videos (image sensor, camera sensor, video sensor, etc.), for sensing a fingerprint, for sensing environmental parameters (e.g. light, temperature), one or more light emitting diode sensors for, e.g., providing visual feedbacks, etc.

The mobile device may further include additional sensors, for example, a proximity sensor for determining the closeness of the mobile device and/or its camera to a user's eye, and the like, a gyroscope sensor for determining the mobile device orientation, or for measuring the rate of the rotation of the mobile device around a particular axis, for example, the user line-of-sight axis, and the like. Therefore, the orientation of the mobile device may be evaluated by its gyroscope sensor and an angular position of the mobile device may be determined.

Moreover, the mobile device may further include an accelerometer sensor for measuring non-gravitational acceleration of the mobile device. In some embodiments, the mobile device or its accelerometer sensor may further be specifically designed to respond to the vibration associated with a movement of the mobile device. Therefore, the movement of the device and/or a linear acceleration of the mobile device may be measured based on its vibration.

The mobile device may further include additional sensors such as an ambient light sensor, additional compass sensors, a barometer sensor, a touch ID fingerprint scanner, an iris motion sensor, etc.

In some embodiments the circuitry may further be configured to, for example, perform a function by simply shaking the mobile device, for example, in the case that a high quality image of a user's eye is captured, the circuitry may perform a shaking of the mobile device or its accelerometer to guide the user, or the like.

The mobile device, the circuitry, or its camera may further be configured to capture an image of a user's eye. The image may be a high resolution image of the user's eye, may be a still image, a video of the user's eye, etc.

In some embodiments, the circuitry may further be configured to provide a video shooting mode, for automatic capturing of the plurality of images. For example, the camera may be placed in the video shooting mode which may enable automatically capturing the plurality of images. Therefore, the user may not need to press a shutter button, or the like.

In some embodiments, the circuitry may further be configured to provide a selfie eye shot mode. Moreover, the user may capture the plurality of images (e.g. from the user's eye) with the camera which is played in selfie shot mode.

In some embodiments, the circuitry may further be configured to analyze the plurality of captured images with a trained model. Moreover, the user instruction may be based on the analysis of the plurality of captured images.

The trained model, may be for example, a model which is trained by feeding high quality images (e.g. captured by a doctor with a professional fundus camera) to a machine learning algorithm which is used for the model, moreover, the model may process the high quality images, and hence, the model may be trained to analyze the plurality of captured images, or the like. The model may include parameters which are determined by the machine learning algorithm during training. The model, the machine learning algorithm and/or the parameters may be stored in the mobile device.

In some embodiments, for example, the trained model may further determine an image quality of at least one feature of the eye in the captured image, and may further be configured to output information for changing the image quality of the at least one feature of the eye.

In some embodiments, changing the image quality may further include improving the image quality of the at least one feature of the eye.

In some embodiments, the trained model may be based on a machine learning algorithm configured to analyze the plurality of captured images. Moreover, the user instruction may be based on the analysis of the plurality of captured images.

As mentioned, the circuitry may further be configured to analyze the captured image with a machine learning algorithm. The machine learning algorithm may further determine an image quality of at least one feature of the eye in the captured image, and may further be configured to output information for changing the image quality of the at least one feature of the eye.

The machine learning algorithm may analyze the captured image based on the feature extraction techniques. The machine learning algorithm may apply an image processing technique, or a pattern recognition technique in which algorithms are used to detect and isolate different features of the eye, or desired portions, in the captured images. The technique might be applied to one or more individual captured images and/or to sequences of captured images and/or to any plurality of captured images.

For example, at least one feature of the eye may be extracted and the image may be analyzed. The extracted features of the eye may be the user's eye retina, the user's eye optic disc, the user's eye blood vessels, the user's eye optic nerve, location of the pupil for at least one of the eyes, physical dimension of the at least one of the eye's pupils, radii of the pupil in the left and right eye, and the like. Such a machine learning algorithm may be based on at least one of: Scale Invariant Feature Transfer (SIFT), Cray Level Co-occurrence Matrix (GLCM), Gaboo Features, Tubeness, or the like.

Moreover, the machine learning algorithm may be based on a classifier technique and the image may be analyzed. Such a machine learning algorithm may be based on least one of: Random Forest; Support Vector Machine; Neural Net, Bayes Net, or the like.

Furthermore, the machine learning algorithm may apply deep-learning techniques and the image may be analyzed. Such deep-learning techniques may be based on at least one of: Autoencoders, Generative Adversarial Network, weakly supervised learning, boot-strapping, or the like.

The machine learning algorithm may determine an image quality of at least one feature of the eye in the captured image. The determination of the image quality might be based on individual captured images and/or on sequences of captured images and/or to any plurality of captured images.

The image quality may be determined based on the image resolution. For example, the location of the eye's pupil may be determined, and the number of the pixels for the location of the pupil in the image may be estimated. Moreover, if the number of pixels exceeds a predetermined threshold value, the image quality may be deemed as sufficient for an eye examination.

Moreover, in some embodiments the image quality may be determined based on detecting at least one feature of the eye in the image. For example, the location of the eye's pupil in the image may be determined, then the physical dimension of the eye's pupil may be estimated, and it may be compared to the physical dimensions of the eye's pupil in a reference image and the image quality may be determined.

In some embodiments, the image quality may be determined based on the environmental parameters, for example, an image may be captured and the ambient light in the captured image may be evaluated. In some embodiments, the image quality may be determined based on the user behavior, for example, in the case that the user blinks, and the like.

Moreover, the image quality may be determined based on the alignment of the camera with the user's eye, for example, with the user's line-of-sight, or the like. For instance, the user should look in a particular direction, the user should focus on an item which is located at a particular distance relative to the eye, and the like.

The image quality may be determined, for example, based on the extraction of the at least one feature of the eye. For instance, the image quality may be determined by the number of pixels in the one feature of the eye in the image and, if the number of pixels exceeds a predetermined threshold value, the image may be used, e.g., for an eye examination. However, if the image quality does not meet the predetermined criterion, the machine learning algorithm may further output information for improving the image quality. The information may be output via an interface and may be obtained by the circuitry and/or it may be provided to the user.

As mentioned, the machine learning algorithm may determine an image quality and may further output information for improving the image quality. Moreover, the circuitry may further output a user instruction, based on the information output by the machine learning algorithm.

For example, the mobile device may capture an image, however, the image quality does not meet a predefined criterion. Moreover, the machine learning algorithm may output information which may instruct the user to improve the image quality.

The user instruction may be based on the information output and the information output may be based on the determined image quality of the at least one feature of the eye. Hence, the user instruction may be based on improving the image quality of at least one feature of the eye, as discussed above.

The user instruction may be based on, for example, improving the image resolution, moving the camera to a certain direction and adjusting the location of the eye's pupil in the image, increasing/decreasing the exposure time, adjusting the ambient light, looking and/or focusing in a certain direction, or the like.

Moreover, the user instruction may be related to the user's behavior, for example, in the case that a user blinks during the time of capturing the image, a user instruction may be output in order to guide the user.

Hence, in some embodiments, it is possible for a user to self-monitor and to self-examine the eye and temporal and/or structural changes on the eye may be automatically detected, based on mobile retinal cameras without having the need to involve an ophthalmologist. By instructing the user to find a position where a high quality image of the eye can be taken, some kind of automatic alignment procedure for the camera or mobile device may be provided. Moreover, a monitoring procedure based on machine learning and image processing techniques may be provided, as discussed above and in the following. In some embodiments, the disclosure helps to monitor changes on the eye in a fully automatic way without the help of an operator, i.e. a patient can monitor and examine his own eye (self-monitoring/self-examination).

Hence, some embodiments are easy to use, are home user friendly, i.e. they are not location bound, save time for user as self-alignment speeds up the setup of the retinal camera of the mobile device, are a cost-effective solution for eye imaging systems, because no second person and/or trained operator is needed. Moreover, automatic alignment enables mobile applications for eye imaging, in some embodiments, monitoring may be independent of an expert and can be handled by anyone without expertise, visits to the doctor may be reduced, possibility of higher screening and monitoring densities may be provided, huge amounts of data for further data processing (i.e. deep learning) may be collected, and/or open up urban regions with a low density of hospitals may be provided with the present self-monitoring/examination solution.

In some embodiments, the user instruction may include a direction movement instruction or an illumination instruction.

The direction movement may be moving the camera upward, downward, left or right, adjusting a distance between the camera and the user's eye by increasing or decreasing the distance, rotating the camera in a certain direction, e.g., a clockwise or a counterclockwise direction, rotating up to a certain angle between an axis of the camera and the user's line-of-sight, and the like. Furthermore, the user instruction may be based on lighting information, for example, based on the ambient light, or a use of a flash light for illuminating the user's eye.

In some embodiments, the user instruction may be output based on haptic information, an acoustic information, or a visual information.

The haptic information/feedback may be, for example, a vibration of the mobile device, which is based on the sense of touch in the mobile device through a user interface.

In one example, the user is moving the mobile camera toward their eye and the mobile device captures still images of the user's eye and the image quality is determined. Moreover, when an image is captured that (almost) meets the image quality of a predetermined criterion, the mobile device vibrates slightly in response to the user's activity (movement of the mobile device towards a certain direction) and the user instruction may be output, for example, to further move the mobile device until an image is captured that meets the image quality of the predetermined criterion.

Moreover, the user instruction may be output based on an acoustic information, for example, via the loudspeakers of the mobile device and the user instruction may be output. In some embodiments the loudspeakers may be a smart speaker that may analyze the plurality of captured images by a cloud computing. For instance, the smart speaker may be connected to a voice-controlled intelligent personal assistant, which may analyze the plurality of captured images or the like.

Likewise, the user instruction may be output based on a visual information, for example, a text instruction may be output via the display of the mobile device. In another embodiment, four light emitting diode sensors may be attached to the mobile device and the direction movement may be provided by illuminating of the corresponding LED sensor. For example, if the user instruction includes an upward movement, an LED sensor which is located on the upper part of the mobile device may be turned on, and the like.

In some embodiments, the capturing of the image, the analyzing of the captured image and the output of the user instruction is performed iteratively.

For instance, the mobile device may capture images from the user's eye, the images may be stored and the image quality may be determined. Moreover, a user instruction may be output and a new image may be captured wherein the new image is captured after the output of the user instruction. Hence, the image quality of the new image may be improved based on the output user instruction. Then, the new image may be stored, and after a user instruction, may be output to improve the image quality of the new image. This iterative process may be repeated until a desired image quality is obtained.

In some embodiments, the iterative performing is done until the image quality of the at least one feature of the eye in the captured image meets a predefined criterion.

The predetermined criterion may be based on, for example, the image resolution, e.g., the number of pixels for a feature of the eye, such as the pupil of the eye. The predefined criterion may relate to the image quality, e.g., location of a feature of the eye in the image, ambient light, sharpness of the image, etc., as discussed above, and the iterative process may be performed until the image quality meets the predefined criterion, which may include that the variation of the image quality is small, e.g. less than a threshold value. For example, the number of pixels of the pupil on the image meet a threshold value, hence, the image resolution may be sufficient for an eye examination.

In some embodiments, the circuitry may further determine a difference between the at least one feature of the eye in the captured image of the user's eye and the at least one feature of the eye in a reference image.

The captured image may be analyzed and the user's eye may be examined. The examination of the user's eye may be based on a comparison of the captured image of the user's eye and a reference image.

In some embodiments, the reference image may be an image that has been captured in the past, for example an image that has been captured by an ophthalmologist. For example, a user visits an ophthalmologist, the ophthalmologist captures a high quality image (e.g. high resolution or the like) of the user's eye, e.g. with a specific Fundus camera or ophthalmoscope, and stores it as a reference image, the reference image may be captured, for example, by an advanced fundus camera.

In some embodiments, the examination may be based on a comparison of a sequence of images or a plurality of images.

Moreover, the user also captures an image by using the camera of the mobile device. The image may be captured, for example, during a treatment procedure and the circuitry may further be configured to determine a difference between the at least one feature of the eye in the captured image of the user's eye and the at least one feature of the eye in the reference image. The difference may be determined based on a temporal variation between the at least one feature of the eye in the captured image of the user's eye and the at least one feature of the eye in the reference image in which both images, the captured image and the reference image, are captured from the user's identical eye.

Moreover, the reference image may be, for example, a high quality image of the user's eye that is captured by the camera of the mobile device and stored as a reference image, e.g., for examination of the user's eye.

Moreover, in some embodiments, the circuitry may further determine a structural change between the user's left and right eye. For instance, the user captures an image from the left eye and stores it as a reference image. Afterwards, the user captures a new image from, for example, the user's right eye and the circuitry may determine a structural variation between the at least one feature of the eye in the captured image of the user's right eye and the at least one feature of the eye in the reference image, which has been captured from the user's left eye.

Moreover, the reference image may be an image, which is captured in a specific condition and is stored as the reference image in order to be used for the user's eye examination at a later time, for example, during a later stage of treatment, or the like.

In some embodiments, the circuitry may further provide a notification, based on the determined difference between the at least one feature of the eye in the captured image of the user's eye and the at least one feature of the eye in the reference image.

The notification may be provided to the user, to a doctor, to an ophthalmologist, to a remote computer in a hospital, or the like. The notification may be a text message, an email, an audio message, or a vibration of the mobile device, or the like. The notification may further include, for example, the result of the analysis of the captured image, the determined difference between the at least one feature of the eye in the captured image of the user's eye and the at least one feature of the eye in the reference image. Moreover, the notification may be provided based on a predetermined threshold value. For example, the user may visit a doctor, the doctor may request the user to regularly capture images from their eye so that the circuitry may further analyze the captured images and, if a specific feature of the eye meets a predetermined threshold value, a notification may be sent, for example, to the doctor, or a notification may be provided to the user to visit the doctor, etc.

In some embodiments, the circuitry may further transmit the captured image to a remote computer.

For example, the user may capture images of its eye, moreover, the images may be transmitted to a remote computer. The remote computer may be located at a hospital, at an eye clinic, at a university, or the like. The captured images may further be interpreted by, for example, an ophthalmologist, and hence, a telemedicine-based eye examination may be performed.

In some embodiments, the mobile device may further store the captured image of the user's eye in a database (e.g. the circuitry is further configured to store the captured image in a storage device either included in the circuitry or remotely located in another computer, storage system or the like).

The database may be located on a server computer, it may be in a cloud, on a memory, on a personal computer, or the like. The stored images may further be used as a reference image, etc.

Some embodiments pertain to a method including capturing a plurality of images of a user's eye with the camera, determining based on at least one of the captured images of the eye, an image quality of at least one feature of the eye in the captured image, and outputting a user instruction for changing the image quality of the at least one feature of the eye. The method may be performed by a mobile device as discussed herein, or by any other electronic processing device. The method may include the features of a mobile device as described herein.

The method may further include analyzing the plurality of captured images with a trained model, wherein the user instruction may be based on the analysis of the plurality of captured images. The method may further include analyzing the plurality of captured images with a machine learning algorithm, wherein the user instruction may be based on the analysis of the plurality of captured images. The machine learning algorithm may output information for improving the image quality of the at least one feature of the eye. The method may further include improving the image quality of the at least one feature of the eye. Moreover, the plurality of images may be automatically captured based on a video shooting mode. Furthermore, the plurality of images may be provided based on a selfie shot mode, as discussed above. As mentioned, the method may include outputting a user instruction and the user instruction may be a direction movement instruction, or an illumination instruction. Moreover, the output of the user instruction may be based on a haptic information, an acoustic information, or a visual information, as discussed above. The capturing of the image, the analyzing of the captured image, and the outputting of the user instruction may be performed iteratively by the method, as discussed above. Moreover, the iterative performing may be done until the image quality of the at least one feature of the eye in the captured image meets a predefined criterion, as discussed above. The method may further include determining a difference between the at least one feature of the eye in the captured image of the user's eye and the at least one feature of the eye in a reference image, as discussed above. The method may further include providing a notification, based on the determined difference between the at least one feature of the eye in the captured image of the user's eye and the at least one feature of the eye in the reference image, as discussed above. The method may further include transmitting the captured image to a remote computer, as discussed above. The method may further include illuminating the user's eye during the time of capturing the image of the user's eye, as discussed above. The method may further comprise storing the captured image of the user's eye in a database, as discussed above.

Figure 2:
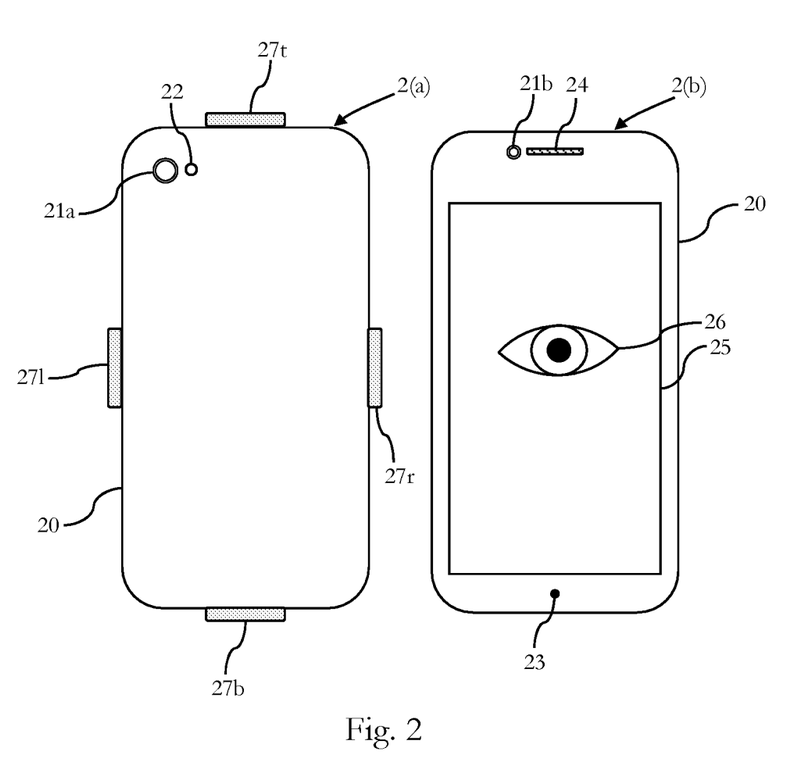
FIGS. 2(a) and 2(b) schematically illustrate an embodiment of a mobile device, which is in the form of a smartphone.
Figure 3:
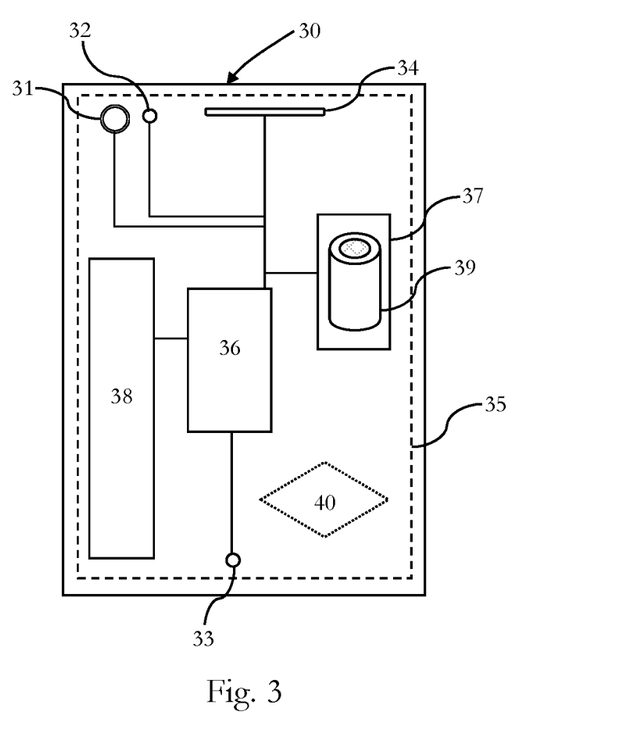
FIG. 3 schematically illustrates an embodiment of the mobile device of FIGS. 2(a) and 2(b)

Returning to FIG. 1, there is illustrated a mobile device 10, a smartphone in this embodiment, which will be presented in more detail in FIGS. 2(a), 2(b) and FIG. 3. The mobile device 10 has a digital camera 11 and a flash light 12 that illuminates the user's eye 13 during the time of capturing an image of the user's eye.

The distance (d) between the user's eye and the mobile device 10 can be adjusted, e.g., by moving the mobile device 10. Moreover, the orientation of the mobile device 10 with respect to the user's eye can be adjusted, e.g., by rotating the angle (θ) between the axis of the camera 11 and the user's line-of-sight.

Light 14 is output from the flash light 12 and illuminates the user's eye during the time of capturing an image of the user's eye 13. The user moves the camera 10 into different positions, which may be different distances, different angles between the axis of the camera and the user's line-of-sight, different ambient or illumination settings, etc. The camera 11 captures still images of the user' eye and stores the captured images in a database 15 which is located on a remote computer 16 and is connected to the mobile device 10 by a wireless connection.

FIGS. 2A and 2B illustrate a mobile device 20, which is in the form of a smartphone. The smartphone 20 has a dual camera system and includes a first camera 21a, which is located on the back side and a second camera 21b, which is located on the front side of the smartphone 20, a flash light 22, which is based on a LED light source, a microphone 23, a(n) speaker/earpiece 24, which is based on a stereo speaker for outputting of, e.g., an acoustic feedback, a touch screen display 25 for receiving the user's input, for example, for transmitting an image of the user's eye or for processing the captured image 26, etc. Moreover, the smartphone 20 is supplied with four LED sensors (27t, 2tb, 27l and 27r), which are located at the top 27t, bottom 27b, left 27l and right 27r sides of the mobile device 20. The LED sensors are used for outputting user instructions, for example, when the camera 21a which is located on the back side of the mobile device 20 is used. The instruction may be a movement of the mobile device 20 to a direction (e.g. left, right, upward, downward) and are output by the corresponding LED sensor in a way that, for example, when the LED sensor 27r, which is located on the right side of the mobile device 20, is turned on, a visual instruction is output, which indicates, the device 20 should be moved in the right direction. The mobile device 20 is illustrated in FIGS. 2A and 2B and discussed in more detail further bellow.

In the following, the mobile device 30 which is in the form of a smartphone is described under the reference of FIG. 3. The smartphone 30, which is similar to the smartphone 20, has a camera sensor 31, an LED sensor 32, a microphone sensor 33, a loud speaker sensor 34 for outputting acoustic instructions, a display 35 which is based on LED-technology and which is configured as a touch screen.

The smartphone 30 has a processor 36 (including one or more processors), which is connected to a storage 37 including a database 39 and an interface 38. The storage 37 includes a random access memory and a flash storage. The interface 38 is adapted to communicate with a mobile telecommunications system, e.g., LTE, GSM, or the like. It is also adapted to perform a wireless communication with a wireless local area network and, for example, to communicate over Bluetooth. Thereby, the smartphone 30 can establish a connection to the internet. Moreover, in the present embodiments, the circuitry includes a machine learning algorithm 40. Note that, the machine learning algorithm may be located in the memory, on the processor, or it may be located on a remote computer, on a server, or the like, without limiting the present disclosure in that regard.

The camera 31, the LED sensor 32, the microphone 33, the loud speaker 34, the display 35, the processor 36, the storage 37, the interface 38, and the machine learning algorithm 40 form a circuitry as discussed herein.

In some embodiments, the smartphone 30 has additional input means, e.g., a keyboard, a touch pad, a gyroscope, an acceleration sensor, a proximity sensor, a compass, etc., as discussed above, without limiting the present disclosure in that regard.

The interface 38 is able to communicate over wire and wirelessly (e.g. Bluetooth and wireless and local area network), such that it can communicate with the internet, a remote computer, a server, a network, an electronic device, e.g., at a hospital, at a doctors' clinic, etc.

The database 39 may include a reference image that may be an image that is captured by a health specialist, such as a doctor, or it may include a reference image or images that have been captured by the camera 31 of the smartphone 30, as discussed above.

In the following an embodiment of an apparatus 50 for capturing an image, analyzing the captured image, determining an image quality with a machine learning algorithm, determining an image quality for the at least one feature of the eye, outputting information for improving the image quality, and outputting a user instruction is discussed under the reference of FIG. 4.

The apparatus 50 includes an image of a user's eye 41, which is captured, for example, by the camera 31 of the smartphone 30.

The image is provided to the machine learning algorithm 40 which may be based on feature extraction techniques without limiting the present disclosure in that regard. The image 41 is provided by the interface 38 of the smartphone 30. The machine learning algorithm 40 determines an image quality of the at least one feature of the eye and outputs information for improving the image quality of the at least one feature of the eye, which may be, for example, the user's eye retina. The output information may be, for example, that the image quality of the user's eye retina can be improved by moving the camera 31 towards the left side of the user's eye. The circuitry receives the output information, for example, by its interface 38 and outputs a user instruction. The user instruction is an acoustic instruction and is output by the loudspeaker 34. The user moves the camera 31 towards their left side, the camera 30 captures a new image and the machine learning algorithm 40 determines an image quality for the user's eye retina and the image quality is improved. Moreover, the smartphone 30 stores the new image in the database 39, which is located on a remote computer 42.

Figure 4:
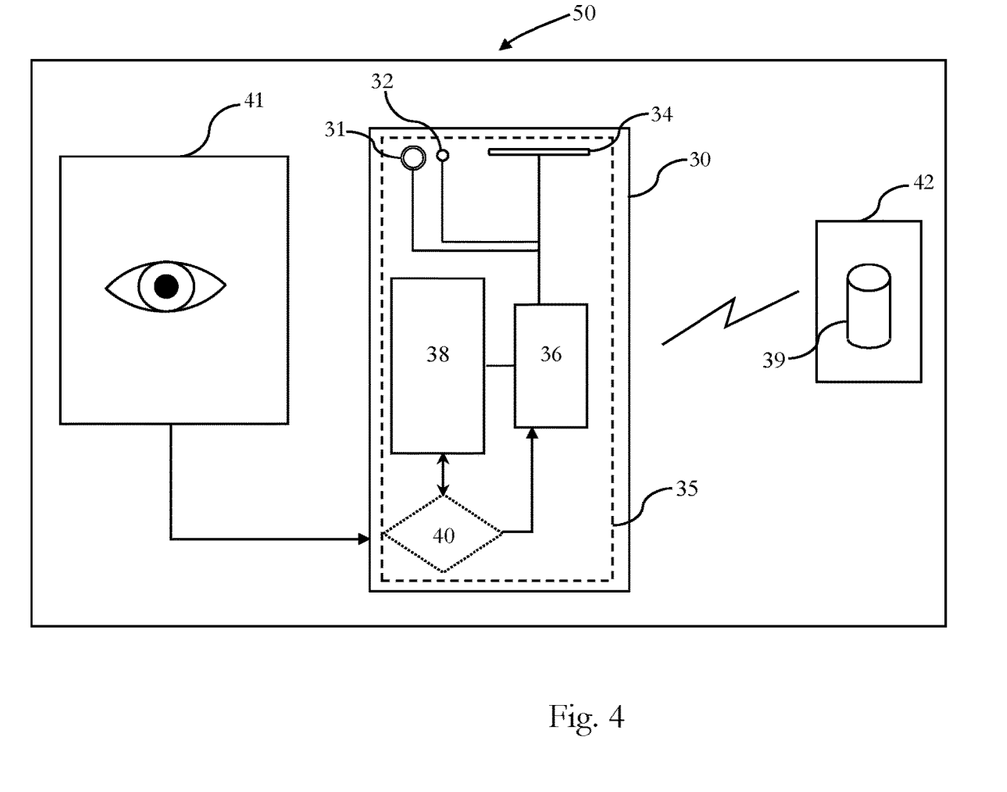
FIG. 4 schematically illustrates an embodiment of an apparatus for capturing an image, analyzing the captured image and determining an image quality with a machine learning algorithm.
Figure 5:
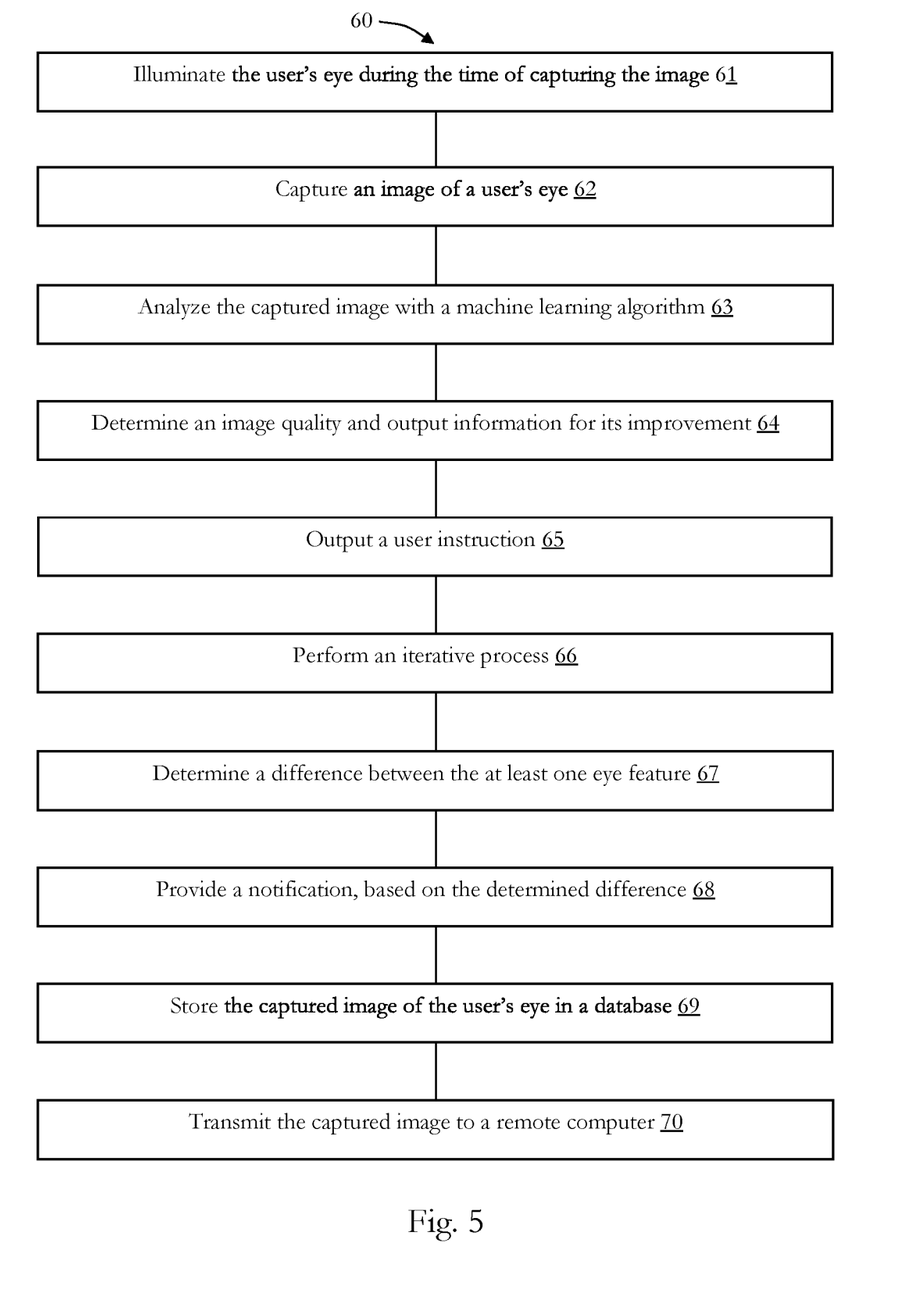
FIG. 5 shows a flowchart illustrating a method, which may be performed by the mobile device.

FIG. 5 shows a method 60 for self-examination of an eye of a user, which may be performed by and with anyone of the devices or apparatus described herein, such as the devices 10, 20 and 30 of FIGS. 1 to 3 and the apparatus 50 of FIG. 4. Without limiting the disclosure, in the following the method 60 is discussed exemplary based on the smartphone 30.

At 61, the smartphone 30 illuminates the user's eye during the time of capturing the image 41 of the user's eye. The user's eye may be illuminated by turning on the LED sensor 32, which is included in the smartphone 30.

At 62, the smartphone 30 captures an image 41 of the user's eye. The image may be captured by the camera 31, which may be located on the back side of the smartphone 30, as discussed above.

At 63, the smartphone 30 analyzes the captured image 41 with a machine learning algorithm 40. The machine learning algorithm may be located on the processor 36 of the smartphone 30. The machine learning algorithm may analyze the image based on the feature extraction technique, as discussed above.

At 64, the machine learning algorithm determines an image quality for at least one feature of the eye in the captured image 41 and outputs information for improving the image quality of the at least one feature of the eye. In the present embodiment, the image quality is determined for the user's eye retina, without limiting the present disclosure in that regard. The machine learning algorithm 40 determines an image quality for the user's eye retina in the captured image 41. Moreover, the machine learning algorithm determines that the image quality of the user's eye retina, for example, can be improved if the user moves the camera closer to the eye. Furthermore, the machine learning algorithm 40 outputs information for improving the image quality of the user's eye retina. The information may be output by the interface 38 and may be obtained by the processor 36 in the smartphone 30, as discussed above.

At 65, the smartphone 30 outputs a user instruction. The user instruction is a direction movement and guiding the user on improving the image quality of the user's eye retina in the captured image 41. The user instruction is an acoustic instruction and may be output by the loud speaker 34, which is included in the smartphone 30, as discussed above.

At 66, the smartphone 30 performs an iterative process. The smartphone captures a new image, wherein the new image is captured after the output of the user instruction. Moreover, the user moves the camera 31 toward the eye and the smartphone 30 captures still images of the user's eye, and smartphone 30 analyzes the captured images, determines an image quality for the user's eye retina in the captured images and outputs the user instructions, as discussed above. This iterative process is performed until the machine learning algorithm 40 determines that the image quality of the user's eye retina meets a predefined criterion, e.g. also by determining that a variation of the image quality of the user's eye retina becomes small (less a threshold), such that a further improvement of the image quality by further aligning the camera 31 is not expected. For example, the user's eye retina in one of the captured images includes a certain number of pixels, hence, the image may be used for eye retina examination.

At 67, the smartphone 30 determines a difference between the at least one feature of the eye in the captured image of the user's eye and the at least one feature of the eye in a reference image. The reference image is an image that has been taken by an ophthalmologist by using a professional fundus camera. The reference image is stored in the database 39, which is located on a remote computer 42. The smartphone 30 determines an image quality for the user's eye retina in the captured image 41 and an image quality for the user's eye retina in the reference image. The image quality is determined by the machine learning algorithm 40, as discussed above. Moreover, the smartphone 30 determines the difference between the image quality of the user's eye retina in the captured image 41 and the user's eye retina in the reference image. Furthermore, the ophthalmologist sets a threshold value for the difference between the image qualities and the smartphone 30 determines that, for example, the difference between the image qualities is above the threshold value, as discussed above.

At 68, the smartphone 30 provides a notification based on the determined difference between the image quality of the user's eye retina in the captured image and the user's eye retina in the reference image. The notification, which is a text message, is provided to the user by displaying it on the display 35 of the smartphone 30, as discussed above.

At 69, the smartphone 30 stores the captured image 41 of the user's eye in the database 39 which is located on the storage 37, as discussed above.

In some embodiments, the captured image may be used as a reference image, as discussed above.

At 70, the smartphone 30 transmits the captured image 41 to a remote computer 42. The smartphone 30 may transmit (e.g. by email) the captured image to a server, and an ophthalmologist may obtain the captured image 41 and may further evaluate the image and examine the user's eye, as discussed above.

Figure 6:
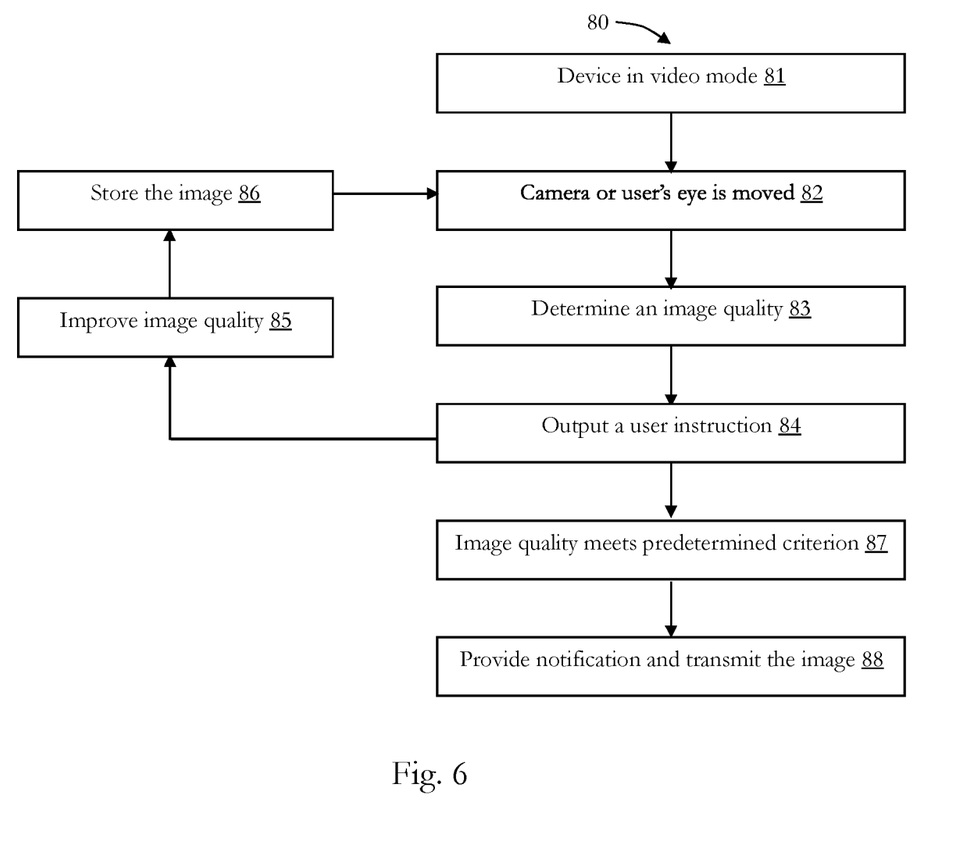
FIG. 6 shows a flowchart illustrating a method for capturing an image of a user's eye.

FIG. 6 shows a method 80 for self-examination of an eye of a user, which may be performed by anyone of the devices or apparatus described herein and without limiting the disclosure, in the following, the method is explained, based on the smartphone 30. According to method 80, an image of the user's eye is captured, wherein the image is captured in an optimal position with respect to the user's eye.

At 81, the mobile device 30, which may be a mobile retinal camera, is set to video mode and, hence, the camera 31 and the flash light 32 face towards the user's eye.

At 82, the user moves the mobile retinal camera 30 into different positions in order to find an optimal position and the camera 31 continuously captures still images of the user's eye.

At 83, the still images are analyzed with a machine learning algorithm, e.g., a regression algorithm, a classification algorithm, etc., and an image quality for the user's eye retina is determined. The user's eye retina in the captured images may be used to monitor changes on the eye and the user's eye may be examined, for example, by an ophthalmologist, as discussed above.

At 84, the mobile retinal camera 30 outputs a user instruction. The output user instruction is a gradual haptic feedback in the form of vibration of the mobile retinal camera and is given to the user with regard to the closeness to the ideal position. The ideal position is a position so that an image can be captured in which the user's eye retina has a quality that can be used for eye examination. Moreover, the image quality is determined with the machine learning algorithm 40, as discussed above. The feedback guides the user to move the mobile retinal camera 30 to the optimal position for capturing the image. The feedback becomes gradually stronger if the mobile retinal camera 30 is moved closer to the optimal position, and becomes weaker if the mobile retinal camera 30 is moved further away.

Moreover, the mobile retinal camera 30 determines an image quality for the captured images, as discussed above, and, if the image quality meets a predefined criterion, goes to 87, and, if the image quality does not meet the predefined criterion, goes to 85.

At 85, the mobile retinal camera 30, captures a new image. The new image is captured after the output of the user instruction and the image quality of the user's eye retina is improved.

At 86, the mobile retinal camera 30 stores the new image in the database 39, as discussed above.

At 87, the mobile retinal camera 30 determines that the image quality of the user's eye retina in the stored image meets the predefined criterion, hence, the image may be used for the user's eye examination.

At 88, the mobile retinal camera 30 provides a notification to the user and transmits the image to the remote computer 42.

Figure 7:
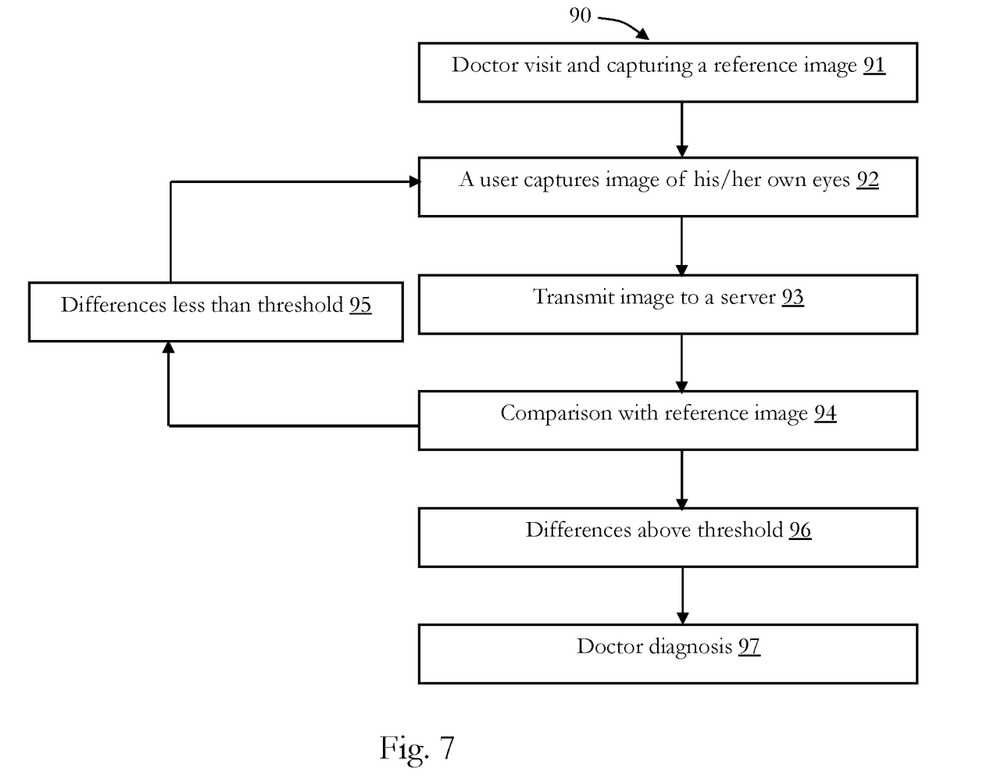
FIG. 7 shows a flowchart illustrating a method, which may be performed by the mobile device for determining a difference between a captured image and a reference image.

FIG. 7 shows a method 90 for self-examination of an eye of a user, which is exemplary explained based on the smartphone 30. Method 90 determines changes on the user's eye relative to a reference image, in particular it determines temporal changes between, for example, the user's left eye with respect to the reference image from the same eye.

Moreover, the method 90 may be performed by the mobile retinal camera 30 for determining the structural changes between, for example, the user's left eye with respect to the reference image in which the reference image is an image that is captured from the user's right eye.

At 91, the user visits a doctor for a first examination. The doctor captures a high quality image of the user's eye and stores it in the database 39 as a reference image.

At 92, the user captures a series of images of their own eyes. The images are captured with the camera 31 of the mobile retinal camera 30, as discussed above.

The user determines an optimal alignment position, as discussed above, e.g. under reference of FIG. 6, and captures images from both their eyes. The images may be used for determining changes between the left and the right eye, as discussed above.

At 93, the captured images are transmitted to a remote computer for further processing based on a tele-medical application.

At 94, the stored reference image in the database 39 is compared to the captured image with the machine learning algorithm and the temporal changes between, for example, the use's eye retina are determined, relative to the reference image.

In some embodiments, the structural changes between the left and the right eye of the user can be determined and the captured images may be used for detecting eye diseases, as discussed above.

Moreover, if the differences between the features of a user's eyes in the captured image and in the reference image are less than a predetermined threshold value, the method goes to 95, and if the difference is above the threshold value it goes to 96.

At 95, if the difference between the image qualities of the features of the user's eye, e.g. the user's retina, is less than a predetermined threshold value, the method further goes to 92 and the user captures a new image of their eye.

At 96, if the difference between the image qualities of the features of the user's eye, e.g. the user's eye retina, is above a predetermined threshold value, for example, a notification may be sent to the user and/or to the doctor. The notification is a text message and may be emailed, for example, to the doctor, as discussed above.

At 97, the user visits the doctor and an eye examination is performed.

The methods as described herein are also implemented in some embodiments as a computer program causing a computer and/or a circuitry and/or a processor to perform the method, when being carried out on the computer and/or a circuitry and/or processor. In some embodiments, also a non-transitory computer-readable recording medium is provided that stores therein a computer program product, which, when executed by a processor, such as the processor described above, causes the methods described herein to be performed.

It should be recognized that the embodiments describe methods with an exemplary ordering of the method. The specific ordering of the method is, however, given for illustrative purposes only and should not be construed as binding. For example, the ordering of 69 and 70 in the embodiment of FIG. 5 may be exchanged. Also, the ordering of 68, 69 and 70 in the embodiment of FIG. 5 may be exchanged. Further, also the ordering of 93 and 94 in the embodiment of FIG. 7 may be exchanged. Other changes of the ordering of the method may be apparent to the skilled person.

Please note that the division of the mobile device 30 into units 31 to 39 is only made for illustration purposes and that the present disclosure is not limited to any specific division of functions in specific units.

All units and entities described in this specification and claimed in the appended claims can, if not stated otherwise, be implemented as integrated circuit logic, for example, on a chip, and functionality provided by such units and entities can, if not stated otherwise, be implemented by software.

In so far as the embodiments of the disclosure described above are implemented, at least in part, using software-controlled data processing apparatus, it will be appreciated that a computer program providing such software control and a transmission, storage or other medium by which such a computer program is provided are envisaged as aspects of the present disclosure.

Note that the present technology can also be configured as described below.

(1) A mobile system, including circuitry including a camera, the circuitry being configured to:

capture a plurality of images of a user's eye with the camera;

determine, based on at least one of the captured images of the eye, an image quality of at least one feature of the eye in the captured image; and output a user instruction for changing the image quality of the at least one feature of the eye.

(2) The mobile system of (1), wherein the circuitry is further configured to analyze the plurality of captured images with a trained model, and wherein the user instruction is based on the analysis of the plurality of captured images.

(3) The mobile system of (1) or (2), wherein the circuitry is further configured to provide a video shooting mode, for automatic capturing of the plurality of images.

(4) The mobile system of anyone of (1) to (3), wherein the circuitry is further configured to provide a selfie eye shot mode.

(5) The mobile system of anyone of (1) to (4), wherein the user instruction includes a direction movement instruction or an illumination instruction.

(6) The mobile system of anyone of (1) to (5), wherein the output of the user instruction is based on a haptic information, an acoustic information, or a visual information.

(7) The mobile system of anyone of (1) to (6), wherein the capturing of the image, the analyzing of the captured image and the output of the user instruction is performed iteratively.

(8) The mobile system of anyone of (1) to (7), wherein the iterative performing is done until the image quality of the at least one feature of the eye in the captured image meets a predefined criterion.

(9) The mobile system of anyone of (1) to (8), wherein the circuitry is further configured to determine a difference between the at least one feature of the eye in the captured image of the user's eye and the at least one feature of the eye in a reference image.

(10) The mobile system of anyone of (1) to (9), wherein the circuitry is further configured to provide a notification, based on the determined difference between the at least one feature of the eye in the captured image of the user's eye and the at least one feature of the eye in the reference image.

(11) The mobile system of anyone of (1) to (10), wherein the circuitry is further configured to transmit the captured image to a remote computer.

(12) The mobile system of anyone of (1) to (11), wherein the circuitry further comprises a light adjacent to the camera for illuminating the user's eye during the time of capturing the image of the user's eye.

(13) The mobile system of anyone of (1) to (12), wherein the circuitry is further configured to store the captured image of the user's eye in a database.

(14) The mobile system of anyone of (1) to (13), wherein changing the image quality comprises improving the image quality of the at least one feature of the eye.

(15) The mobile system of anyone of (1) to (14), wherein the trained model is based on a machine learning algorithm configured to analyze the plurality of captured images, and wherein the user instruction is based on the analysis of the plurality of captured images.

(16) A method including:

capturing a plurality of images of a user's eye with a camera;

determining, based on at least one of the captured images of the eye, an image quality of at least one feature of the eye in the captured image; and outputting a user instruction for changing the image quality of the at least one feature of the eye.

(17) The method of (16), wherein the method further comprises analyzing the plurality of captured images with a trained model, and wherein the user instruction is based on the analysis of the plurality of captured images.

(18) The method of (16) or (17), wherein the plurality of images is automatically captured based on a video shooting mode.

(19) The method of anyone of (16) to (18), wherein the plurality of images is provided based on a selfie shot mode.

(20) The method of anyone of (16) to (19), wherein the user instruction includes a direction movement instruction or an illumination instruction.

(21) The method of anyone of (16) to (20), wherein the output of the user instruction is based on a haptic information, an acoustic information, or a visual information.

(22) The method of anyone of (16) to (21), wherein the capturing of the image, the analyzing of the captured image, and the outputting of the user instruction is performed iteratively.

(23) The method of anyone of (16) to (22), wherein the iterative performing is done until the image quality of the at least one feature of the eye in the captured image meets a predefined criterion.

(24) The method of anyone of (16) to (23), wherein the method further comprises determining a difference between the at least one feature of the eye in the captured image of the user's eye and the at least one feature of the eye in a reference image.

(25) The method of anyone of (16) to (24), wherein the method further comprises providing a notification, based on the determined difference between the at least one feature of the eye in the captured image of the user's eye and the at least one feature of the eye in the reference image.

(26) The method of anyone of (16) to (25), wherein the method further comprises transmitting the captured image to a remote computer.

(27) The method of anyone of (16) to (26), wherein the method further comprises illuminating the user's eye during the time of capturing the image of the user's eye.

(28) The method of anyone of (16) to (27), wherein the method further comprises storing the captured image of the user's eye in a database.

(29) The method of anyone of (16) to (28), wherein changing the image quality comprises improving the image quality of the at least one feature of the eye.

(30) The method of anyone of (16) to (29), wherein the trained model is based on a machine learning algorithm configured to analyze the plurality of captured images, and wherein the user instruction is based on the analysis of the plurality of captured images.

(31) A computer program including program code causing a computer to perform the method according to anyone of (16) to (30), when being carried out on a computer.

(32) A non-transitory computer-readable recording medium that stores therein a computer program product, which, when executed by a processor, causes the method according to anyone of (16) to (30) to be performed.

(33) An apparatus including circuitry configured to perform the method of anyone of (16) to (30).

(34) A mobile system including;
   capturing means for capturing a plurality of images of a user's eye;
   determining means for determining, based on at least one of the captured images of the eye, an image quality of at least one feature of the eye in the captured image; and
   outputting means for outputting a user instruction for changing the image quality of the at least one feature of the eye.

(35) A method including;
   a step of capturing a plurality of images of a user's eye;
   a step of determining, based on at least one of the captured images of the eye, an image quality of at least one feature of the eye in the captured image; and
   a step of outputting a user instruction for changing the image quality of the at least one feature of the eye.

(36) A computer program including program code causing a computer to function as;
   capturing means for capturing a plurality of images of a user's eye;
   determining means for determining, based on at least one of the captured images of the eye, an image quality of at least one feature of the eye in the captured image; and
   outputting means for outputting a user instruction for changing the image quality of the at least one feature of the eye.

(37) A non-transitory computer-readable recording medium that stores therein a computer program product, which, when executed by a processor, causes the computer to function as;
   capturing means for capturing a plurality of images of a user's eye;
   determining means for determining, based on at least one of the captured images of the eye, an image quality of at least one feature of the eye in the captured image; and
   outputting means for outputting a user instruction for changing the image quality of the at least one feature of the eye.

The invention claimed is:

1. A system, comprising:
   circuitry configured to:
      obtain a plurality of images of a user's eye captured by a camera;
      determine, based on at least one of the captured images of the eye, an image quality of at least one feature of the eye in the captured image;
      output a user instruction, based on the determined image quality, for changing the image quality of the at least one feature of the eye;
      iteratively determine the image quality of the captured image and output the user instruction until the image quality of the at least one feature of the eye in the captured image meets a predefined criterion;
      determine a difference between the at least one feature of the eye in the captured image meeting the predetermined criterion and the at least one feature of the eye in a reference image previously captured of the eye; and
      provide a notification, when the determined difference exceeds a threshold, that includes an indication of a structural change between the at least one feature of the eye in the captured image of the user's eye and the at least one feature of the eye in the reference image.

2. The system of claim 1, wherein the circuitry is further configured to analyze the plurality of captured images with a trained model, and wherein the user instruction is based on the analysis of the plurality of captured images.

3. The system of claim 1, wherein the circuitry is further configured to provide a video shooting mode, for automatic capturing of the plurality of images.

4. The system of claim 1, wherein the circuitry is further configured to provide a selfie eye shot mode.

5. The system of claim 1, wherein the user instruction includes a direction movement instruction or an illumination instruction.

6. The system of claim 1, wherein the output of the user instruction is based on a haptic information, an acoustic information, or a visual information.

7. The system of claim 1, wherein the circuitry is further configured to transmit the captured image to a remote computer.

8. The system of claim 1, wherein the circuitry further comprises a light adjacent to the camera for illuminating the user's eye during the time of capturing the image of the user's eye.

9. The system of claim 1, wherein the circuitry is further configured to store the captured image of the user's eye in a database.

10. The system of claim 1, wherein changing the image quality comprises improving the image quality of the at least one feature of the eye.

11. The system of claim 2, wherein the trained model is based on a machine learning algorithm configured to analyze the plurality of captured images, and wherein the user instruction is based on the analysis of the plurality of captured images.

12. A method comprising:
   obtaining a plurality of images of a user's eye captured by a camera;
   determining, based on at least one of the captured images of the eye, an image quality of at least one feature of the eye in the captured image;
   outputting a user instruction, based on the determined image quality, for changing the image quality of the at least one feature of the eye;
   iteratively determining the image quality of the captured image and outputting the user instruction until the image quality of the at least one feature of the eye in the captured image meets a predefined criterion;
   determining a difference between the at least one feature of the eye in the captured image meeting the predetermined criterion and the at least one feature of the eye in a reference image previously captured of the eye; and
   provide a notification, when the determined difference exceeds a threshold, that includes an indication of a structural change between the at least one feature of the eye in the captured image of the user's eye and the at least one feature of the eye in the reference image.

13. The method of claim 12, wherein the method further comprises analyzing the plurality of captured images with a trained model, and wherein the user instruction is based on the analysis of the plurality of captured images.

14. The method of claim 12, wherein the plurality of images is automatically captured based on a video shooting mode.

15. The method of claim 12, wherein the plurality of images is provided based on a selfie shot mode.

16. The method of claim 12, wherein the user instruction includes a direction movement instruction or an illumination instruction.

17. The method of claim 12, wherein the output of the user instruction is based on a haptic information, an acoustic information, or a visual information.

18. The method of claim 12, wherein the method further comprises transmitting the captured image to a remote computer.

19. The method of claim 12, wherein the method further comprises illuminating the user's eye during the time of capturing the image of the user's eye.

20. The method of claim 12, wherein the method further comprises storing the captured image of the user's eye in a database.

21. The method of claim 12, wherein changing the image quality comprises improving the image quality of the at least one feature of the eye.

22. The method of claim 13, wherein the trained model is based on a machine learning algorithm configured to analyze the plurality of captured images, and wherein the user instruction is based on the analysis of the plurality of captured images.

* * * * *